United States Patent [19]
Narayanan et al.

[11] Patent Number: 5,834,400
[45] Date of Patent: Nov. 10, 1998

[54] EMULSIFIABLE CONCENTRATE FOR A LOW DOSAGE FLUORINATED AGRICULTURAL CHEMICAL

[75] Inventors: Kolazi S. Narayanan; Ronald H. Goehner, Jr., both of Wayne, N.J.

[73] Assignee: ISP Investments Inc., Wilmington, Del.

[21] Appl. No.: 846,963

[22] Filed: Apr. 29, 1997

[51] Int. Cl.$^6$ .......... A01N 25/30; A01N 43/40; A01N 47/40

[52] U.S. Cl. .......... 504/116; 504/130; 504/257

[58] Field of Search .......... 504/116, 130, 504/257

[56] References Cited

U.S. PATENT DOCUMENTS

| | | | |
|---|---|---|---|
| 5,436,223 | 7/1995 | Mulqueen et al. | 504/128 |
| 5,605,876 | 2/1997 | Higashimura et al. | 504/103 |

*Primary Examiner*—S. Mark Clardy
*Attorney, Agent, or Firm*—Walter Katz; Marilyn J. Maue; William J. Davis

[57] ABSTRACT

An effective emulsifiable concentrate for a low dosage fluorinated agricultural chemical, e.g. diflufenican, a herbicide, in optional admixture with a diluent active agricultural chemical, e.g. bromoxynil octanoate or isooctyl-metachlorophenyl acetate herbicides is described herein.

6 Claims, No Drawings

EMULSIFIABLE CONCENTRATE FOR A LOW DOSAGE FLUORINATED AGRICULTURAL CHEMICAL

BACKGROUND OF THE INVENTION

1. Field of the Invention

This invention relates to liquid delivery systems for active agricultural chemicals, and, more particularly, to an emulsifiable concentrate for delivering an admixture of a low dosage fluorinated agricultural chemical and a diluent active agricultural chemical to a plant site.

2. Description of the Prior Art

Emulsion concentrates are favored liquid delivery systems for active agricultural chemicals. See Narayanan U.S. Pat. Nos. 5,231,070; 5,298,529; 5,317,042; and 5,389,297.

An emulsifiable concentrate (EC) is a solution of the agchemical, solvents and surfactants that when diluted with water forms an emulsion which can be sprayed onto crops. An EC is needed for most agchemicals because they are usually water insoluble. Such concentrates are easy to store and transport, and various adjuvants may be added to increase the efficacy of the formulation. A good EC, however, requires that a stable emulsion be formed upon dilution with water, which emulsion does not separate upon standing. Furthermore, there should not be any crystallization of the active from the EC after water dilution. In addition, the EC itself must be stable with little degradation of the active over a long shelf life, and over a range of storage temperatures.

A poor EC is generally recognized by poor emulsion stability wherein the micelles of the emulsion are observed to coalesce upon water dilution, and by rapid crystal formation therein. For such ECs, it is necessary to add a crystal inhibitor, or, more likely, to reformulate the EC. A suitably reformulated EC thus must solubilize the active in a suitable solvent system which must also be sufficiently hydrophobic so that the active remains in the micelle and does not migrate into the water phase of the emulsion.

Accordingly, it is an object of this invention to provide an effective EC for an admixture of a low dosage, water-insoluble fluorinated active agricultural chemical and a diluent agricultural chemical.

These and other objects and features of the invention will be made apparent from the following more particular description of the invention.

SUMMARY OF THE INVENTION

What is provided herein is an EC for an admixture of a low dosage, water-insoluble fluorinated active agricultural chemical, such as diflufenican herbicide, and, optionally, a diluent active agricultural chemical such as bromoxynil octanoate or isooctyl-metachlorophenyl acetate herbicides which includes by weight, (a) about 20–60% of such an admixture of low dosage active and diluent active; (b) about 2–15% of an anionic surfactant, such as an ethoxylated nonyl phenol phosphate ester; optionally including 0–10% of a non-ionic surfactant, such as ethoxylated castor oil; and (c) about 15–30% of a $C_6$–$C_{18}$ alkyl pyrrolidone; optionally including 0–10% of a $C_1$–$C_4$ alkyl pyrrolidone or gamma-butyrolactone, and 0–30% of a $C_6$–$C_8$ alkyl acetate.

DETAILED DESCRIPTION OF THE INVENTION

In accordance with the invention, the primary active agricultural chemical which has been formulated into a useful EC, is an admixture of a low dosage, water-insoluble fluorinated agricultural chemical, such as diflufenican, and, optionally, a diluent active agricultural chemical, such as bromoxynil octanoate. A typical admixture in the EC formulation includes about 2.6% diflufenican and about 37.1% bromoxynil octanoate. Other active agricultural chemicals as secondary diluents also may be included within this mixture if desired.

The EC composition thus includes (a) about 20–60% of the admixture of active agricultural chemicals; (b) about 2–15% of an anionic surfactant, suitably an ethoxylated nonyl phenol phosphate ester; optionally with up to about 10% of a non-ionic surfactant, suitably an ethoxylated castor oil; (c) about 15–30% of a $C_6$–$C_{18}$ alkyl pyrrolidone, most suitably N-octyl pyrrolidone, N-isooctyl pyrrolidone or N-dodecyl pyrrolidone, or mixtures thereof, N-octyl pyrrolidone being preferred, optionally including up to 10% of a $C_1$–$C_4$ alkyl pyrrolidone or gamma-butyrolactone, and optionally up to 30% of a $C_6$–$C_8$ alkyl acetate.

EXAMPLES OF FLUORINATED ACTIVE INGREDIENTS AND DILUENTS (A) Fluorinated active ingredients Fluorinated Herbicides/Insecticides Herbicides FLURTAMONE (Chevron)

FLUMETSULAM (Dow Elanco)

CLODINAFOP-PROPARGYL (Ciba Geigy)

THIAZOPYR (Monsanto/Rhom AND Haas)

FLURPRIMIDOL (Dow Elanco)

ETHOXYFEN-ETHYL (Budapest Chemical)

FLUTHIACET-METHYL (Kumiai Chemical/Ihara Chemical)

SULFENTRAZONE (FMC)

FLUPOXAM (Kureha Chemical/Monsanto)

FLUMIOXAZIN (Sumitomo)

ISOXAFLUTOLE (FMC)

CARFENTRAZONE-ETHYL (FMC)

Herbicides (Diluents):

METOLACHLOR (Ciba Geigy)

TRIFLURALIN (Dow Elanco)

CHLOPYRALID (Dow Elanco)

2,4, D (Several Companies)

CLODINAFOP-PROPARGYL (Ciba Geigy)

ISOPROTURON (Rhone Poulenc)

DIURON (Rhone Poulenc)

DSMA (Disodium Methane Arsonate), and MSMA (Monosodium Methane Arsonate)

Insecticides

FIPRONIL (Rhone Poulenc)

FLUFENOXURON (Ciba Geigy)

FLUVALINATE (Sandoz)

FLUCYTHRINATE (Du Pont)

CYFLUTRRIN (Bayer)

TEFLUTHRIN (ICI)

BIFENTHRIN (FMC)
DIFLUBENZURON (Duphar, Netharlands)
TRIFLUMURON (Bayer)
CHLORFLURAZUM (Ciba Geigy/Ishihara)
Insecticides (Diluents)
CARBARYL (Rhone Poulenc)
PERMETHRIN (Several)
PIPERONYL BUTOXIDE (Several)
HYDRAMETHYLNON (Am. Cy)
DIAZINON (Ciba Geigy)
ALDECARB (Union Carbide)
Fungicides
FLUOROMIDE (Mitsubhishi)
FLUTRIAFOL (ICI)
FLUTOLANIL (Nihaku Nohyaku, Japan)
FLUSILAZOL (Du Pont)
TRIFLUMIZOLE (Nippon Soda Co)
Fungicide (Diluents)
PROPICONAZOLE (Ciba Geigy)
PENCONAZOLE (Ciba Geigy)
TRIFORINE (CelamercK, Germany)

THIABENDAZOLE (Merck)
DACONIL (ISK Biotech)
MANCOZEB (Rhom and Haas)
Plant Growth Regulators/Repellents/Rodenticides
FLUMETRALIN (Ciba Geigy)
FLURPRIMIDOL (Dow Elanco)
EFLUIDIDE (3M)
FLURAZOLE (Monsanto)
BROMETHALIN (Eli Lilly)
Plant Growth Regulators/Repellents/Rodenticides—Diluents
THIRAM (TETRAMETHYL THIURAM DISULFIDE) —(Du Pont)
ETHEPHON (Rhone Poulenc)

The EC compositions thus-prepared are shown in Table 1 below. The degree of stability of such EC compositions upon dilution with water (1:50) is given in Table 2 below.

TABLE 1

EC COMPOSITIONS OF INVENTION

|   |   | (1) | (2) | (3) | (4) | (5) |
|---|---|---|---|---|---|---|
| (a) | Diflufenican | 2.6 | 2.6 | 2.6 | 2.8 | 2.6 |
|   | Bromoxynil octanoate | 37.1 | 37.1 | 37.1 | — | 37.1 |
|   | MCPA Iso-octylester | — | — | — | 42.0 | — |
| (b) | Nonyl phenol ethoxylated phosphate ester |   |   |   |   |   |
|   | (Rhodofac ® RE610) | 5.0 | 5.0 | 5.0 | — | 5.0 |
|   | (Rhodofac RM 710) | — | — | — | 6.0 | — |
|   | Ethoxylated castor oil |   |   |   |   |   |
|   | (Alkamuls ® EL 719) | 5.0 | 5.0 | 5.0 | 6.0 | 5.0 |
| (c) | N-Octyl pyrrolidone |   |   |   |   |   |
|   | (Agsol ® EX 8) | 22.6 | 22.6 | 25.2 | 25.9 | 25.2 |
|   | N-Methyl pyrrolidone |   |   |   |   |   |
|   | (Agsol ® EX 1) | — | 5.1 | — | 4.3 | — |
|   | Aromatic petroleum distillate |   |   |   |   |   |
|   | (Aromatic 200) (Exxon) | 5.1 | — | — | — | 20.1 |
|   | Heptyl acetate |   |   |   |   |   |
|   | (Exxate 700) (Exxon) | 22.6 | 22.6 | 25.1 | 13.0 | — |
|   | gamma-butyrolactone (BLO) | — | — | — | — | 5.0 |

TABLE 2

Stability of EC Compositions Upon Dilution with Water ((1:50)

|   | Appearance | | | | |
|---|---|---|---|---|---|
|   | (1) | (2) | (3) | (4) | (5) |
| Initial bloom | Excellent | Excellent | Excellent | Excellent | Excellent |
| After 20 inversions | Excellent | Excellent | Excellent | Excellent | Excellent |
| After 24 hrs | Excellent (sl. trace ppt) | Excellent (sl. trace ppt) | Excellent (sl. trace ppt) | Excellent | Excellent (sl trace ppt) |
| After 4 days | Excellent (Trace ppt) | Excellent (Trace ppt) | Excellent (Trace ppt) | Excellent | Excellent (sl trace ppt) |

What is claimed is:

1. An emulsifiable concentrate (EC) which forms an aqueous micelle emulsion upon dilution with water in a 1:50 wt. ratio, which remains stable towards crystal formation during storage for at least 4 days comprising, by weight:
   (a) about 20–60% of an admixture of a low dosage, water-insoluble fluorinated active agricultural chemical and a diluent active agricultural chemical,
   (b) about 2–15% of an anionic surfactant and up to about 10% of a non-ionic surfactant, said surfactant system being sufficiently hydrophobic to keep the actives within the micelles instead of migrating into the water phase of the emulsion,
   (c) about 15–30% of a $C_6$–$C_{18}$ alkyl pyrrolidone, and at least one of the following: up to about 10% of a $C_1$–$C_4$ alkyl pyrrolidone or gamma-butyrolactone, up to about 30% of a $C_6$–$C_8$ alkyl acetate or an aromatic petroleum distillate.

2. An EC according to claim 1 wherein said admixture comprises diflufenican as the fluorinated active agricultural chemical and bromoxynil octanoate and/or isooctyl metachlorophenyl acetate as the diluent active agricultural chemical.

3. An EC according to claim 1 wherein said anionic surfactant is an ethoxylated nonyl phenol phosphate ester.

4. An EC according to claim 1 wherein said non-ionic surfactant is an ethoxylated castor oil.

5. An EC according to claim 1 wherein said $C_6$–$C_{18}$ alkyl pyrrolidone is N-octyl pyrrolidone.

6. An EC according to claim 1 wherein said $C_1$–$C_4$ alkyl pyrrolidone is N-methyl pyrrolidone.

* * * * *